US005635596A

United States Patent [19]
Chambon et al.

[11] Patent Number: 5,635,596
[45] Date of Patent: Jun. 3, 1997

[54] PEPTIDES DERIVED FROM THE PS2 PROTEIN

[75] Inventors: Pierre Chambon, Blaesheim; Marie-Christine nee Martinet Rio, Illkirch-Graffenstaden; Jean-Pierre Bellocq, Strasbourg, all of France

[73] Assignee: Aderegem, Paris, France

[21] Appl. No.: 989,886

[22] Filed: Dec. 10, 1992

Related U.S. Application Data

[63] Continuation of Ser. No. 360,906, filed as PCT/FR88/00531 Oct. 28, 1988 published as WO89/03845 May 5, 1989 abandoned.

[30] Foreign Application Priority Data

Oct. 30, 1987 [FR] France ................... 87 15060

[51] Int. Cl.$^6$ ............... A61K 38/00; C07K 14/00; C07K 16/00; C07K 16/30
[52] U.S. Cl. ............ 530/324; 530/300; 530/325; 530/388.8; 530/388.85
[58] Field of Search ............ 530/324, 300, 530/350, 387.7, 325, 388.8, 388.85; 514/12

[56] References Cited

U.S. PATENT DOCUMENTS 5,202,417  4/1993  Hayashi ................... 530/324

FOREIGN PATENT DOCUMENTS 0118365  9/1984  European Pat. Off. .

OTHER PUBLICATIONS von Heijne Eur J Biochem 133 1983 pp. 17–21 Patterns of Amino Acids Near Signal–Sequence Cleavage Sites.
Cloning of a Gene Expressed in Human–Breast Cancer and Regulation By Estrogen In MCF–7 Cell pp. 11–21 Prud'Homme et. DNA 1985 vol. 4.
Mairesse et al Biochem & Bioph. Res Com vol. 97 1980, pp. 1251–1257—Estrogen–Induced Protein In the Human Breast Cancer Cell Line MCF–7.
Sofer Biotechniques. vol. 1 pp. 198–203 1983 Designing an Optimal Chromatographic Purification Scheme for Proteins.
Scopes—Protein Purification & Practice, Springer–Verlag pp. 55–62 1980.
Nucleic Acids Research, vol. 15, No. 4, Feb. 25, 1987, IRL Press, Oxford–Washington DC, J.J. Jeltsch et al.: "Structure of the Human Oestrogen–Responsive Gene pS2", pp. 1401–1414.
Science, vol. 241, Aug. 5, 1988, M.C. Rio et al.: "Breast Cancer—Associated pS2 Protein: Synthesis and Secretion By Normal Stomach Mucosa", pp. 705–708.
Annals of the New York Academy of Sciences, vol. 464, 1986, The New York Academy of Sciences, B. Gairard et al.: "Estrogen–Inducible Gene In Human Breast Cancer", pp. 443–447.
Perlman et al, J Mol. Biol 167: 391–409, "A Putative Signal Peptidase Recognition Site & Sequence in Eukaryotic & Prokaryotic Signal Peptides".
Lerner et al, The Biology of Immunologic Disease pp. 331–338, 1983 The Development of Synthetic Vaccines, Chapter 31.
Brown et al, PNAS 81: 6344–6348, 1984, "Activation of Ps2 Gene Transcription Is a Primary Response to Estrogen In the Human Breast Cancer Cell Line MCF–7".
Jakowlew et al NAR 12: 2861–2878, "Sequence of the Ps2 In RNA Induced By Estrogen In the Breast Cancer Cell Line MCF–7".
Nunez et al, Endocrinology, 121: 1759–1765 Nov. 1987 "Characterization of the Estrogen–Induced pS2 Protein Secreted By the Human Breast Cancer Cell Line MCF–7."
Mori et al, Biochem. & Biophys. Res Comm. 155: 366–372 Aug. 1988, "Identification of a Polypeptide Secreted By Human Breast Cancer Cells (MCF–7) As the Human Estrogen–Responsive Gene (pS2) Product."

*Primary Examiner*—Hazel F. Sidberry
*Attorney, Agent, or Firm*—Oblon, Spivak, McClelland, Maier & Neustadt, P.C.

[57] ABSTRACT

Peptides derived from the pS2 protein and polyclonal and monoclonal antibodies directed against pS2 and against pS2 fragments. Method of obtaining the secreted from of the pS2 protein and fragments thereof. Method of detecting and diagnosing different pathological conditions and especially hormone-dependent breast cancers and pathological conditions of the stomach.

1 Claim, 6 Drawing Sheets

PEPTIDES DERIVED FROM THE PS2 PROTEIN

This application is a continuation of application Ser. No. 07/360,906, filed Jun. 9, 1989, abandoned, which was filed as International Application No. PCT/FR88/00531 on Oct. 28, 1988.

BACKGROUND OF THE INVENTION

1. Field of the Invention

The present invention relates to the identification of the sequence of the pS2 protein secreted in different human tissues and humors, and to peptide fragments of this protein; the present invention further relates to polyclonal and monoclonal antibodies directed against pS2 and against peptide fragments of the pS2 protein, and to the applications of this protein and these peptides and antibodies to the diagnosis and detection of various pathological conditions and especially hormone-dependent breast cancers and stomach cancers or ulcers.

2. Discussion of the Background

The fact that breast cancer is hormone-dependent has been known since 1896, when Beatson [Lancet (1986), 2, 104–107] reported two observations of the regression of inoperable tumors after ovariectomy in women who were still having menstrual periods. It is now well established that about one third of breast cancers respond to hormones and regress following a variety of hormonal manipulations.

Until recent years, there was no biochemical test for identifying women who were suffering from hormone-dependent cancer and who could therefore benefit from endocrinotherapy. In 1971, Jensen et al. [NATL. CANCER INSTI. MONOGR. (1971) 34, 55–70] were the first to show that measurement of the estrogen receptors in a tumor specimen could be useful for predicting the response to adrenalectomy. This observation has since been amply confirmed as 50 to 65% of women whose tumors contain estrogen receptors (ER's) respond to endocrinotherapy, whereas those whose tumors do not contain estrogen receptors have only a 10% chance, at best, of being helped by hormone treatment.

In fact, if cancerous cells possess sites having a strong affinity for a hormone (i.e. a receptor), such sites normally being present in the mammary gland, their growth, like that of normal cells, can be regulated by the hormonal environment. Conversely, if cancerous cells lose their receptors during the malignant transformation, they are no longer recognized as target cells. However, the result of determination of the estrogen receptors (ER's) does not permit a perfect prediction of the response to hormonotherapy as only 55% to 65% of women whose tumors possess receptors respond favorably to hormone treatment. One of the explanations lies in the fact that, in the course of dedifferentiation, some tumors may lose their estrogen receptors. If these receptors persist, the tumors may retain the capacity to bind estradiol, but are incapable of carrying through the subsequent steps of the estrogenic action. Both cases involve tumors which are hormonally autonomous or hormone-resistant. This last hypothesis was proved by going beyond the initial step, i.e. binding to the cytosol receptor, and investigating the end products of the intracellular action of estrogens. This is the case, for example, of the progesterone receptor (PR) as its synthesis is dependent on estrogens in MCF-7 cells (cell line derived from a human breast cancer) and probably in human breast cancer cells in vivo. In actual fact, if the proportion of progesterone receptors is taken into account, the remission levels of cancers under hormone treatment are of the order of 65%. Numerous clinical trials have established that 80% of women whose tumors possess both receptors respond to hormonotherapy. By contrast, if the tumor contains estrogen receptors but not progesterone receptors, the probability of response is no more than one third of cases. The progesterone receptors (PR's) therefore provide additional information for prediction of the therapeutic response.

Estrogens stimulate the synthesis of a large number of proteins which are released in the incubation medium of cell lines such as MCF-7. Most of the proteins secreted are detected in the incubation medium with or without estradiol, but their activity is very considerably increased if this hormone is present. They correspond to molecular weights of 37,000, 46,000, 54,000 and 60,000M [MAIRESSE et al. in RECENT RESULTS IN CANCER RESEARCH, G. LECLERCQ, S. TOMA, R. PARIDAENS, J. C. HEUSEN, vol. 91, (1984) 301–306]. Some of them (46,000, 54,000 and 60,000M) are identical to the cytosol proteins. A protein of 50,000M is more abundant in the incubation medium treated with estradiol, but MAIRESSE's work demonstrates that this involves stimulation of the secretion of this protein under the action of a hormone, rather than induction. Furthermore, these stimulated proteins also exist in the incubation medium of MCF-7 cells and are also present in the incubation medium of estrogen-independent Evsa-T cells, but the estradiol in this last medium has no effect on the syntheses and/or their secretion. This is not therefore a case of the induction of a new product under hormonal influence, but only an increase in the concentration of an existing product.

ROCHEFORT (same publication as above, p. 289–294) detected a high level of 52K protein in the incubation medium and showed that the induction of this protein was specific for the action of estradiol at physiological concentrations, whereas progesterone and dexamethasone were inactive. Tamoxifen, which inhibits cell growth, does not induce secretion of the 52K protein and prevents the action of estradiol in a molar ratio of 10. One of its metabolites, monohydroxytamoxifen, is 200 times more active than tamoxifen in blocking cell growth and the secretion of 52K in MCF-7 cells. More recently, this same team found that in a variant of MCF-7 cells, namely R-27 cells, which possess ER's and PR's but whose growth escapes the action of estrogen inhibitors, the 52K protein continues to be secreted in the presence of tamoxifen or monohydroxytamoxifen.

A team of researchers, including some of the inventors of the present patent application, set out to achieve the expression of specific genes. Starting with a cDNA library built up from MCF-7 cells induced by estradiol, it was possible to carry out differential cloning of the cDNA's corresponding to the mRNA synthesized in the presence of this hormone. With the aid of a cDNA probe produced from cells growing in the presence and absence of hormone, a cDNA clone corresponding to an mRNA which is present only in MCF-7 cells cultivated in the presence of estradiol could be isolated. It was called pS2. The authors deduced, from the determination of the nucleotide sequence of the cloned cDNA, that it is a protein comprising 84 amino acids and having a low molecular weight of 9140 Daltons [JAKOWLEW et al., It should be recalled that sequence (I), determined for the pS2 protein from mRNA, comprises 84 amine acids, has a molecular weight of the order of 9140 Daltons and is as follows:

| 1   |     |     |     |     |     |     |     |     | 10  |     |     |     |     |
|-----|-----|-----|-----|-----|-----|-----|-----|-----|-----|-----|-----|-----|-----|
| MET | ALA | THR | MET | GLU | ASN | LYS | VAL | ILE | CYS | ALA | LEU | VAL | LEU |
|     |     |     |     |     | 20  |     |     |     |     |     |     |     |     |
| VAL | SER | MET | LEU | ALA | LEU | GLY | THR | LEU | ALA | GLU | ALA | GLN | THR |
|     | 30  |     |     |     |     |     |     |     |     |     | 40  |     |     |
| GLU | THR | CYS | THR | VAL | ALA | PRO | ARG | GLU | ARG | GLN | ASN | CYS | GLY |
|     |     |     |     |     |     |     | 50  |     |     |     |     |     |     |
| PHE | PRO | GLY | VAL | THR | PRO | SER | GLN | CYS | ALA | ASN | LYS | GLY | CYS |
|     |     |     | 60  |     |     |     |     |     |     |     |     |     | 70  |
| CYS | PHE | ASP | ASP | THR | VAL | ARG | GLY | VAL | PRO | TRP | CYS | PHE | TYR |
|     |     |     |     |     |     |     |     |     | 80  |     |     |     |     |
| PRO | ASN | THR | ILE | ASP | VAL | PRO | PRO | GLU | GLU | GLU | CYS | GLU | PHE |
|     |     |     |     |     |     |     |     |     |     |     |     |     | (I) |

NUCLEIC ACIDS RES. (1984) 12, 2861–2878]. The hormonal regulation exerted on the pS2 gene is situated at the transcriptional level. The gene is not transcribed in the absence of estradiol, whereas there is a distinct accumulation of mRNA eight hours after the hormone has been added to the culture medium. However, the authors had not yet isolated the pS2 protein. Estradiol-induced screening of the cDNA library built up from MCF-7 cells made it possible also to isolate two other clones, 36 B4 and 3 A5. No hormonal regulation is exerted at the transcriptional level of their corresponding gene. These two clones were called "constant" clones. The 36 B4 and 3 A5 probes can therefore be used to assess the amount of total mRNA's present, whereas the pS2 probe corresponds to a specific estrogen-induced RNA of MCF-7 cells. pS2 RNA is not present in the RNA extracted from T 47 D human breast cancer cells, which contain both estrogen and progesterone receptors but in which the presence of the latter receptor is constitutive. Conversely, 36 B4 RNA is present in T 47 D cells.

JELTSCH et al. [NUCLEIC ACID RES. (1987), 15, p. 1401–1414] subsequently cloned the human pS2 gene from DNA of placental cells and cells of the MCF-7 line, studied its structure and established and hence verified the nucleotide sequence of the pS2 gene on the basis of the pS2M clone obtained from the said cell line, and on the basis of the pS2P clone obtained from placental cells.

The observation that pS2 RNA is expressed in the MCF-7 cell line derived from a human breast cancer, but is not expressed in the T 47D cell line, indicates a method of identifying hormone-dependent breast cancers. It is for this reason that the inventors attempted to check whether the expression of the pS2 gene can constitute an additional marker for the detection of hormone-dependent breast cancers.

More recently [RIO et al., SCIENCE (1988) 241, p. 705–707], the pS2 protein was detected in the mucosa cells of the gastric epithelium. The protein secreted in the gastric fluid has an identical electrophoretic migration to that observed for the protein secreted by MCF-7 cells, and the work reported in the article cited above shows that the size and sequence of the mRNA's isolated from the two tissues are strictly identical.

Now, the inventors have been able to establish that this is not the secreted form of the pS2 peptide.

SUMMARY OF THE INVENTION

The object of the present invention is consequently to identify the actual complete primary sequence of the pS2 peptide secreted in different tissues, so that it can be produced by genetic engineering, especially by synthesis in an appropriate vector and an appropriate host, and to raise antibodies which can be used, inter alia, for the detection and diagnosis of pathological conditions.

DRAWINGS

FIG. 3a–F shows that the peptide (D) staining test was found to be cytoplasmic both on sections of breast cancer cells and on sections of metastatic nodes.

DESCRIPTION OF THE PREFERRED EMBODIMENTS

The present invention relates to a peptide which consists of a fragment corresponding to 60 amino acids of the protein of sequence (I) identified above, corresponds to the secreted form, starts with the sequence GLU-ALA-GLN, GLU being located in position twenty-five downstream of the N-terminal MET of the protein of sequence (I) initially identified, and has a molecular weight of about 6600 Da.

According to the present invention, the pS2 peptide of 60 amino acids has the following sequence (D):

| GLU | ALA | GLN | THR | GLU | 30 THR | CYS | THR | VAL | ALA | PRO | ARG | GLU | ARG |
|-----|-----|-----|-----|-----|-----|-----|-----|-----|-----|-----|-----|-----|-----|
| | 40 | | | | | | | | | | | 50 | |
| GLN | ASN | CYS | GLY | PHE | PRO | GLY | VAL | THR | PRO | SER | GLN | CYS | ALA |
| | | | | | | | 60 | | | | | | |
| ASN | LYS | GLY | CYS | CYS | PHE | ASP | ASP | THR | VAL | ARG | GLY | VAL | PRO |
| | | | 70 | | | | | | | | | | 80 |
| TRP | CYS | PHE | TYR | PRO | ASN | THR | ILE | ASP | VAL | PRO | PRO | GLU | GLU |
| GLU | CYS | GLU | PHE | | | | | | | | | | |

(D)

Also according to the present invention, the peptide of sequence (D) comprises four trypsin cleavage sites which are located downstream of the basic amino acids $Arg_{36}$, $Arg_{38}$, $Lys_{54}$ and $Arg_{63}$.

The present invention further relates to so-called "trypsin peptides" obtained by cleavage of the peptide of sequence (D) at the trypsin cleavage sites.

Among these trypsin peptides, the invention encompasses the following in particular:

- a trypsin peptide corresponding to the 12 N-terminal amino acids of the peptide of sequence (D),
- a trypsin peptide corresponding to the amino acid sequence running from $GLN_{39}$ to $LYS_4$,
- a trypsin peptide corresponding to the amino acid sequence running from $GLY_{55}$ to $ARG_{63}$, and
- a trypsin peptide corresponding to the 21 C-terminal amino acids of the said peptide.

The present invention further relates to a peptide which constitutes the signal peptide when the pS2 protein is secreted, especially in the case of breast cancers and pathological conditions of the stomach, and comprises the 24 N-terminal amino acids of the pS2 protein.

The present invention further relates to a peptide which consists of a fragment corresponding to the 31 C-terminal amino acids of the peptide of sequence (D) and has a molecular weight of about 3450 Da.

The present invention further relates to a peptide which consists of a fragment corresponding to the 30 N-terminal amino acids of the peptide of sequence (D) and has a molecular weight of about 3300 Da.

The present invention further relates to a peptide which consists of a fragment corresponding to the 28 amino acids of the C-terminal end of the peptide of sequence (D) and has a molecular weight of about 3100 Da.

According to the present invention, the signal peptide has the following amino acid sequence (G):

| 1 MET | ALA | THR | MET | GLU | ASN | LYS | VAL | ILE | 10 CYS | ALA | LEU | VAL | LEU |
|-----|-----|-----|-----|-----|-----|-----|-----|-----|-----|-----|-----|-----|-----|
| | | | | | 20 | | | | | | | | |
| VAL | SER | MET | LEU | ALA | LEU | GLY | THR | LEU | ALA | | | | |

(G)

According to the present invention, the peptide fragments called "trypsin peptides" correspond to the following amino acid sequences (H), (J), (K) and (L):

|     |     |     |     |     | 30  |     |     |     |     |     |     |     |
| --- | --- | --- | --- | --- | --- | --- | --- | --- | --- | --- | --- | --- |
|     | GLU | ALA | GLN | THR | GLU | THR | CYS | THR | VAL | ALA | PRO | ARG |
|     | 40  |     |     |     |     |     |     |     |     | 50  |     |     | (H) |
| GLN | ASN | CYS | GLY | PHE | PRO | GLY | VAL | THR | PRO | SER | GLN | CYS | ALA |
| ASN | LYS |     |     |     |     |     |     |     |     |     |     |     | (J) |
|     |     |     | GLY | CYS | CYS | PHE | ASP | 60 ASP | THR | VAL | ARG |     | (K) |
|     |     |     |     |     |     | 70  |     |     |     |     |     |     |
| GLY | VAL | PRO | TRP | CYS | PHE | TYR | PRO | ASN | THR | ILE | ASP | VAL | PRO |
|     |     | 80  |     |     |     |     |     |     |     |     |     |     |
| PRO | GLU | GLU | GLU | CYS | GLU | PHE |     |     |     |     |     |     | (L) |

According to the invention, the composition (C) of the peptide comprising 31 amino acids is as follows:

|     |     |     |     |     |     | 60  |     |     |     |     |     |     |     |     |
| --- | --- | --- | --- | --- | --- | --- | --- | --- | --- | --- | --- | --- | --- | --- |
| LYS | GLY | CYS | CYS | PHE | ASP | ASP | THR | VAL | ARG | GLY | VAL | PRO | TRP | CYS |
|     | 70  |     |     |     |     |     |     |     |     |     | 80  |     |     |     |
| PHE | TYR | PRO | ASN | THR | ILE | ASP | VAL | PRO | PRO | GLU | GLU | GLU | CYS | GLU |
| PHE |     |     |     |     |     |     |     |     |     |     |     |     |     | (C) |

Also according to the invention, the composition (E) of the peptide comprising 30 amino acids is as follows:

|     |     |     |     |     | 30  |     |     |     |     |     |     |     |
| --- | --- | --- | --- | --- | --- | --- | --- | --- | --- | --- | --- | --- |
| GLU | ALA | GLN | THR | GLU | THR | CYS | THR | VAL | ALA | PRO | ARG | GLU | ARG |
|     | 40  |     |     |     |     |     |     |     |     | 50  |     |     |     |
| GLN | ASN | CYS | GLY | PHE | PRO | GLY | VAL | THR | PRO | SER | GLN | CYS | ALA |
| ASN | LYS |     |     |     |     |     |     |     |     |     |     |     | (E) |

Also according to the invention, the composition (F) of the peptide comprising 28 amino acids is as follows:

|     |     |     | 60  |     |     |     |     |     |     |     |     |     | 70  |
| --- | --- | --- | --- | --- | --- | --- | --- | --- | --- | --- | --- | --- | --- |
| CYS | PHE | ASP | ASP | THR | VAL | ARG | GLY | VAL | PRO | TRP | CYS | PHE | TYR |
|     |     |     |     |     |     |     |     |     | 80  |     |     |     |     |
| PRO | ASN | THR | ILE | ASP | VAL | PRO | PRO | GLU | GLU | GLU | CYS | GLU | PHE |
|     |     |     |     |     |     |     |     |     |     |     |     |     | (F) |

The present invention further relates to anti-pS2 polyclonal antibodies which are obtained by the immunization of rabbits or other appropriate animals against the pS2 protein and its fragments.

The present invention further relates to anti-pS2 monoclonal antibodies which are obtained by the cloning of hybridomas resulting from the fusion of spleen cells of appropriate mammals immunized by suitable injections of the pS2 protein or fragments thereof, with cells of an appropriate myeloma.

Of course, any other methods of obtaining monoclonal antibodies are included in the framework of the present invention provided they make it possible to obtain the anti-pS2 monoclonal antibodies which are protected within the framework of the present invention.

The present invention further relates to a method of obtaining the peptide of formula (D) purified from a fluid of biological origin, wherein the proteins contained in this fluid are precipitated with acetone at low temperature, especially at about −20° C., and the residue containing the peptide is purified by chromatography in order to recover the fractions containing the peptide, which are frozen and/or concentrated if desired.

In one way of carrying out the method of obtaining the peptide of formula (D) according to the present invention, prior to purification of the fluid of biological origin, MCF-7 cells are taken and cultured in the presence of estradiol and the culture supernatant is collected, freed of the essential debris which it contains and then subjected to the above-mentioned purification process.

In another way of carrying out the method of obtaining the peptide of formula (D) according to the invention, the biological fluid used is gastric juice containing the said peptide secreted by the gastric tissues, which is neutralized with an appropriate buffer at about pH 9.6 before being subjected to the above-mentioned purification process.

In an advantageous way of carrying out the method of obtaining the peptide of formula (D), the latter is isolated by immunopurification from biological fluids or from extracts of cells containing the said peptide, with the aid of antibodies directed against the pS2 protein or against fragments thereof.

The present invention further relates to a method of preparing the pS2 protein and fragments thereof by means of synthesis, especially by chemical synthesis or biosynthesis.

It is possible in particular to use the solid phase method developed by MERRIFIELD (MERRIFIELD's method is described in "Special Methods in Peptide Synthesis" published in 1980 by E. GROSS and J. MEIENHOPER in "THE PEPTIDES: Analysis, Synthesis, Biology", vol. 2, part A, p. 1–254, Academic Press, New York) or any other synthetic method (biosynthesis, especially by genetic engineering).

The present invention further relates to a method of detecting and diagnosing the pathological condition of an organ which causes the peptide of formula (D), its precursors or its fragments to be expressed by the said organ, wherein the presence of one of these peptides is determined by an immunological method in biological specimens with the aid of antibodies directed against one of the said peptides.

In another way of putting the invention into effect, the detection and diagnosis are performed on body fluids.

In one advantageous embodiment of the method of detection and diagnosis according to the invention, the expression of the pS2 gene is determined by immunocytochemistry.

In another advantageous embodiment of the said method of detection, the expression of the pS2 gene is determined in tumor specimens.

In yet another advantageous embodiment of the method of detection and diagnosis according to the invention, the tumor specimens used can be, inter alia, histological sections or cytosols.

According to an advantageous provision of this embodiment, the tumor specimens used are histological sections preserved and stabilized by embedding in paraffin and fixed with formalin, which give the diagnostic method a very high degree of sensitivity and a low background and preserve the histopathological structure.

In one advantageous embodiment of the method of detection and diagnosis according to the invention, given by way of example, the immunocytochemical method is carried out by incubation of the said specimens with polyclonal or monoclonal antibodies of a rabbit (or other appropriate animal) which are directed against pS2 or against pS2 fragments, this being preceded by incubation with serum of a sheep (or other appropriate animal) to reduce the non-specific staining, and followed by several successive incubations with anti-rabbit sheep IgG's and then with an appropriate system for labeling and revealing the antibody.

According to an advantageous provision of the invention, the said system for labeling and revealing the antibody can comprise a rabbit PAP (peroxidase-antiperoxidase) system with which the said specimens are then incubated, after which they are incubated with DAB (3,3'-diaminobenzidine hydrochloride), these operations being followed, if desired, by staining of the section with hematoxylin or the like, the resulting stain being estimated on a stain intensity scale and the proportion of stained tumoral cells being determined as a percentage of the total tumoral cells (1–100%), while the staining index is obtained by multiplying the percentage of stained cells by the staining score (1–300).

The invention further relates to a ready-to-use kit for detecting and diagnosing the pathological condition of an organ by immunocytochemistry, which comprises:

appropriate doses of polyclonal or monoclonal antibodies directed against the pS2 protein and/or its fragments;

appropriate doses of the pS2 protein and/or those of its fragments against which the antibodies used are directed;

appropriate doses of antibodies directed against immunoglobulins of a rabbit (or other appropriate mammal);

an enzyme system (such as PAP (peroxidase-antiperoxidase system) in particular) for developing the antibody-antigen reaction;

a substrate for developing the enzyme reaction, such as DAB in particular;

if desired, a substance for staining the tumoral cells if the biological specimen consists of histological sections and if it is desired to stain them; and useful amounts of appropriate buffers for performing the detection and diagnostic test.

It is of course possible to use any other appropriate system for labeling and revealing the antibody by a direct or indirect method (especially by the sandwich method, by means of the avidin and biotin labeling systems, by fluorescence, phosphorescence, proteinate, RIA, ELISA, etc.).

Although the hormone-dependence of certain breast cancers is well known, the majority of patients presenting tumors containing ER's (estrogen receptors), although not all, can benefit from hormone treatment. On the other hand, the fact that 30 to 40% of patients presenting ER-rich cancers give a negative response to hormone treatment has been attributed either to the heterogeneity of the tumor or to the fact that the ER's may not be functional. Moreover, it has been suggested that the determination of the proportion of PR's (progesterone receptors), whose expression is known to be estrogen-dependent in normal reproductive tissues and in the MCF-7 cell line derived from a breast cancer, could make it possible to identify tumors possessing functional receptors. In fact, not all ER(+) and PR(+) breast cancers respond to hormonotherapy (only 80% respond), which shows the need to have additional markers for response to hormonotherapy in order to permit easier identification of those breast cancers which might benefit from hormonotherapy.

In an advantageous embodiment of the method of detection and diagnosis according to the invention, biological specimens used for the detection of a breast tumor are subjected to simultaneous immunocytochemical detection of the ER's, the PR's and the pS2 protein or one of its fragments, revealing on the one hand an additional functional heterogeneity in ER(+) breast cancers (with only about 60% of ER(+) tumors also being positive for the PR's and the expression of the pS2 gene) and on the other hand a great homogeneity of ER(−) cancers as regards the PR's and the expression of the pS2 gene (with about 96% absence of expression of these two genes inducible by estrogens).

According to an advantageous provision of this embodiment, the ER and PR immunocytochemical detection tests are performed on histological sections frozen at −180° C., preferably in isopentane.

The practical techniques for the immunocytochemical detection of ER's and PR's are known and are described in the literature.

In another way of putting the invention into effect, pathological conditions of the stomach, especially cancers and ulcers, are detected and diagnosed.

In fact, the inventors have detected the presence of the peptide of sequence (D) in tumors of stomach cancers.

This observation makes it possible in particular to detect and diagnose stomach cancers and to determine the origin of metastases.

According to the invention, the method of detection and diagnosis is applied to the in vivo determination of pathological conditions of an organ by immunoscintigraphy with the aid of the antibodies according to the invention.

The present invention further relates to therapeutic agents which contain one or more antibodies according to the present invention.

According to the invention, the said antibodies can be associated with another therapeutic agent.

In addition to the foregoing provisions, the invention also includes other provisions which will become apparent from the following description.

The invention will be understood more clearly with the help of the following additional description, which refers to practical Examples of the subjects of the invention without in any way implying a limitation.

It must be clearly understood, however, that these practical Examples are given solely in order to illustrate the subjects of the invention and do not in any way imply a limitation.

EXAMPLE 1

Purification of peptide (D) produced by MCF-7 cells

MCF-7 cells are cultivated in the presence of $10^{-9}$M estradiol for 4 days.

The culture supernatant, enriched in peptide (D) secreted in the culture medium by the said cells, is collected and subjected successively to the action of:

acetone (IV) at $-20°$ C. in order to precipitate high-molecular proteins, and

12N HCl (at about pH 1) in order to precipitate the proteins which are insoluble at this pH.

The two precipitates are centrifuged successively in order to remove the residues and retain only the supernatants containing peptide (D). This supernatant is treated with 4 volumes of acetone at $-20°$ C. in order to precipitate the other proteins present, including peptide (D). After centrifugation, the supernatant is removed and the residue containing peptide (D) is collected.

The residue is lyophilized; 3 ml of KCl buffer, 50 mM EDTA, are added to the lyophilizate; the mixture is subjected successively to HPLC on G 3000 and reversed-phase HPLC.

120 fractions, each of 1.5 ml, are recovered and subjected to western blotting (immunofingerprint) The fractions containing peptide (D) are identified with the aid of rabbit polyclonal antibody directed against a synthetic peptide corresponding to the 31 C-terminal amino acids of peptide (D).

The positive fractions are pooled, subjected a second time to reversed-phase HPLC of the BROWNLEE-AQUAPORE RP 300 type and then frozen at $-20°$ C. or concentrated by centrifugation under vacuum. The sample is checked on SDS-polyacrylamide gel and revealed by staining of the proteins with silver nitrate.

80% pure peptide (D) is isolated.

EXAMPLE 2

Purification, from gastric juice, of peptide (D) secreted by stomach mucosa cells Gastric juice is collected from fasting individuals (pH 1), neutralized with carbonate/bicarbonate buffer at pH 9.6 and centrifuged to remove the debris.

The supernatant is subjected to the action of:

acetone at $-20°$ C. in a proportion of 4 volumes of acetone per volume of supernatant.

After centrifugation, the supernatant is removed and the residue, which contains peptide (D), is collected and lyophilized.

This residue is subjected to HPLC on G3000. The fractions recovered are identified by western blotting and the positive fractions are pooled and concentrated by centrifugation under vacuum. They are then subjected a second time to reversed-phase HPLC of the BROWNLEE-AQUAPORE RP 300 type and the positive fractions are identified by dot-blot and reconcentrated by centrifugation under vacuum.

EXAMPLE 3

Synthesis of the protein of formula I and its fragments, especially the peptides of formulae (C), (D), (E) and (F)

Each of these substances is synthesized using MERRIFIELD's solid phase method. After lyophilization, the synthesized protein or peptides are respectively reduced in the presence of a urea/β-mercaptoethanol mixture, salted out to remove the salts, and relyophilized, and their amino acid composition is verified.

EXAMPLE 4

Preparation of polyclonal antibodies with the aid of the peptide of formula (C)

Peptide (C), composed of the 31 amino acids at the carboxy-terminal end of protein (I) and synthesized according to Example 3, is injected subcutaneously into rabbits 3 times at 2-week intervals, in an amount of 200 μg, the said peptide being mixed with Freund's complete adjuvant for the first two injections. The serum was collected two weeks after the last injection and used at an appropriate dilution.

Using the same method, polyclonal antibodies are prepared from all the fragments of protein (I) and especially from the peptides of formulae (D), (E) and (F).

EXAMPLE 5

Preparation of specific monoclonal antibodies

A) Immunization of the mice

Biozzi mice were immunized with the synthetic peptide of sequence (F), which corresponds to the 28 amino acids of the C-terminal end of the pS2 protein.

The first two injections were carried out with peptide (F) (100 μg) coupled with ovalbumin by means of glutaraldehyde (F-OVA, Neosystem Laboratory). The coupling ratio obtained is 25 mol of peptide (F) per mol of ovalbumin. The injections were then continued with peptide (F) (100 μg) by itself. The injections were carried out every 15 days and were all given intraperitoneally, with the addition of Freund's complete adjuvant for the first injection and Freund's incomplete adjuvant for the second and third injections. 10 days after the third injection, a drop of blood is taken from the animal's eye and the serum obtained after coagulation is tested by RIA against purified and iodized peptide (D). If the serum titer is correct, the mouse is reinjected twice, two days and four days before fusion.

If the serum titer is not correct, the mouse is reinjected every three weeks until the test is positive.

B) Preparation of the hybridomas

Fusion was carried out in the presence of PEG with X63 myeloma cells in a proportion of two spleen cells per myeloma cell. The hybridomas obtained were distributed into 3 plates of 24 wells. The hybridomas can be selected by adding HAT to the culture medium four hours after fusion. The cultures were continued in the presence of macrophages. The first tests on culture supernatant were undertaken about 8 days after fusion. The said tests are identical to those performed on the sera, namely using the RIA technique against the native protein. The class of the antibodies produced was also determined by the ELISA technique using second antibodies directed against strict subclass.

13 wells containing one or more hybridomas were selected in this way: 4 of them were cloned, namely CIB3, CIB6, CIC4 and CIIID5. Following the first cloning, the CIC4-12 and CIIID5-20 clones, both of which were RIA-positive, were cloned a second time. After this second cloning, 10 of the 12 colonies subcultured from CIIID5-20 contained the antibody directed against peptide (F). Among these, CIIID5-20-9(p28$_1$0$_2$) was chosen according to culture criteria. As the other cloning detected only 3 positive clones out of 12, a third cloning was carried out in which 11 out of 12 colonies proved positive. As before, one of them was chosen: CIC4-12-4-7(p28$_2$0$_3$).

Some of the clones obtained permit an excellent immunohistochemical detection of the peptide of sequence (D) on the sections of breast cancer biopsies, this detection being identical in all respects to that previously obtained with the polyclonal antibodies directed against the synthetic peptides and especially peptide (c).

C) RIA (radioimmunoassay) for detection of the antibodies directed against peptide (D)

The RIA used to verify the presence of peptide (D) and the selection of the hybridomas was performed as follows:

Peptide (D) was extracted from an MCF-7 culture medium and was then partially purified by repeated HPLC. This gives a fraction containing 80% of peptide (D). This enriched fraction is then labeled with iodine 125 (ORIS Lapam) by the chloramine T method. The labeling yield is of the order of 2000 Ci/mmol.

The iodized peptide (D) is then separated from the free iodine by passage over an affinity column prepared by coupling a rabbit polyclonal antibody with Sepharose CN4B. The peptide is recovered by elution in an HCl-glycine medium, pH 2.8. It is then divided into aliquots and is ready for use.

The test consists in adding the following:

200 µl of PBS BSA 0.3%,

100 µl of $^{125}$I (F) tracer (about 30,000 cpm) and

100 µl of medium containing the antibody to be tested.

The mixture is shaken and left overnight at room temperature.

The following are added the next day:

50 µl of NHS (normal human serum) and

50 µl of AMSS (anti-mouse sheep serum).

The mixture is shaken and left for 15 minutes at room temperature.

It is centrifuged for 15 minutes at 3000 rpm (Jouan) and the residues are counted in a gamma counter.

The following are prepared for each series of tests:

a tube (T) containing only iodized peptide, giving the maximum cpm for the amount used (about 30,000 cpm); and a tube (NBS) to which no solution of anti-D antibody is added, giving the background for the manipulation (about 600 cpm). The test sera are diluted to 1/100 and 1/1000.

EXAMPLE 6

Characterization of the peptide of sequence (D)

Figure 1:
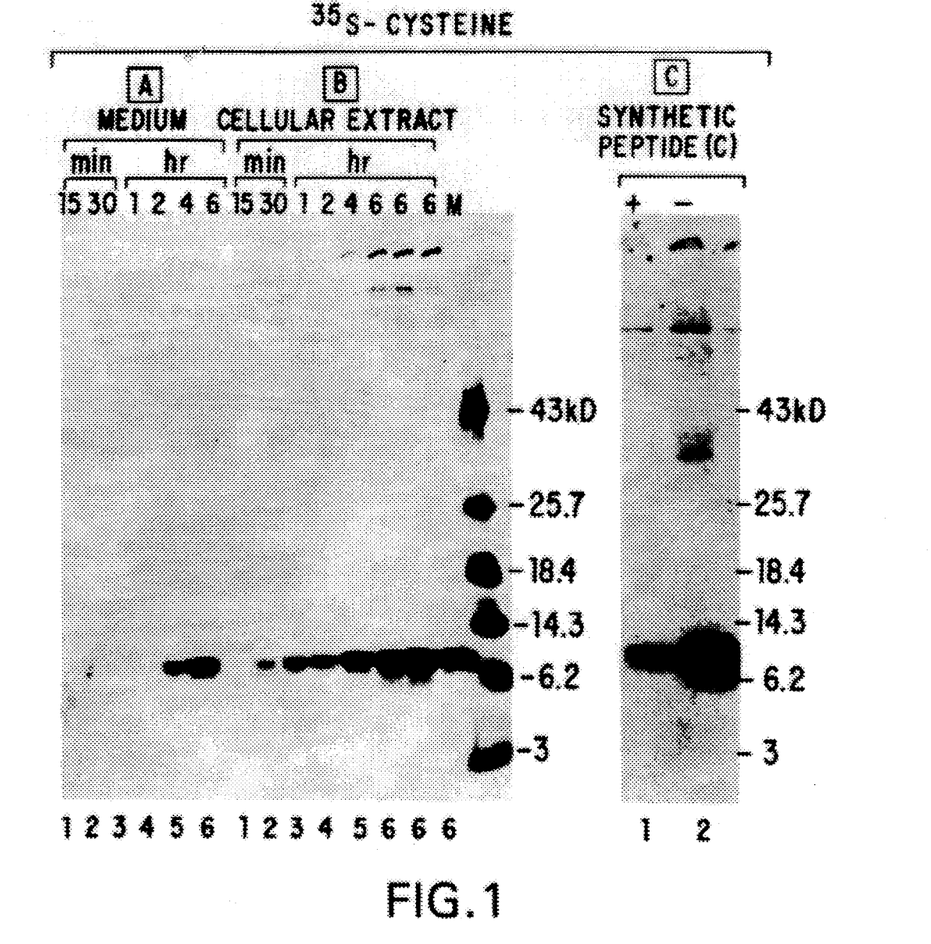
FIG. 1 is an SDS-polyacrylamide gel containing $^{35}$S-methionine labelled pS2 which has been immunoprecipitated with pS2 antiserum.

70 to 90% of confluent monolayers of MCF-7 cells cultivated in the presence of estradiol were labeled with $^{35}$S-cysteine (cf. FIG. 1 attached) or $^{35}$S-methionine (cf. FIG. 2 attached) and the medium together with cellular extracts were collected at fixed intervals. Aliquots were immunoprecipitated with pS2 antiserum and analyzed on a gradient of 15 to 25% of SDS-polyacrylamide gel. The development with time relative to the $^{35}$S-cysteine (FIG. 1, A and B) shows the presence of a single band situated at about 7 KD. In the cellular extract (part B of FIG. 1), the signal is already visible after 15 minutes of labeling. When the samples of medium corresponding to identical aliquots of the total culture medium were analyzed (part A of FIG. 1), the signal became visible after one hour of labeling, which suggests a certain delay in the secretion process. In FIG. 1C, the immunoprecipitation of peptide (D) in the medium (lane 2) is shown as being specific considering that the band of peptide (D) is in competition with synthetic peptide (C) (lane 1).

Figure 2A:
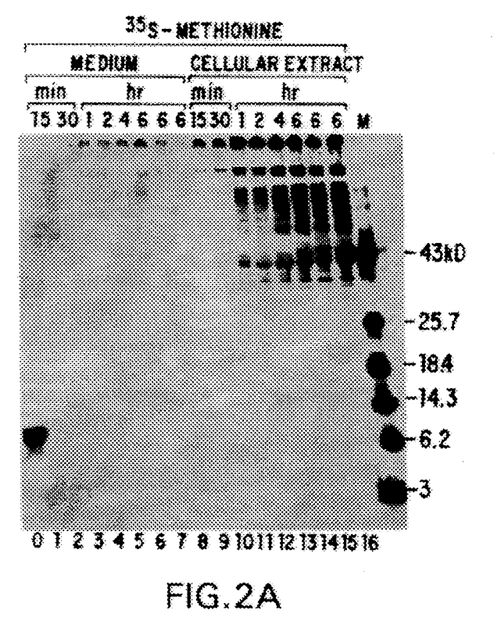
FIG. 2 is an SDS-polyacrylamide gel showing that no band of the size expected for peptide (D) could be detected after labelling with $^{35}$S-methionine and immunoprecipitation with pS2 antiserum.
Figure 2B:
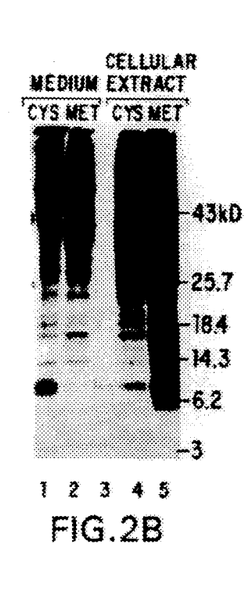
Figure 2C:
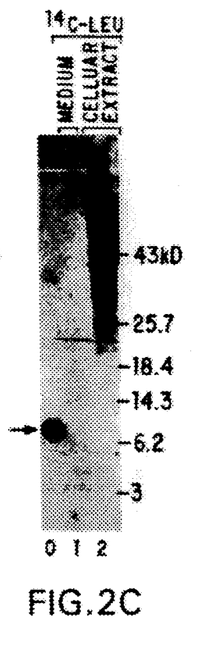
Figure 3A:
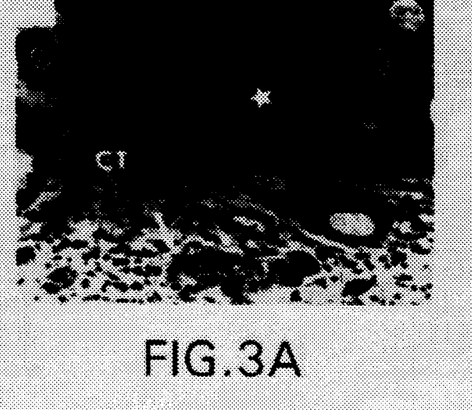
Figure 3B:
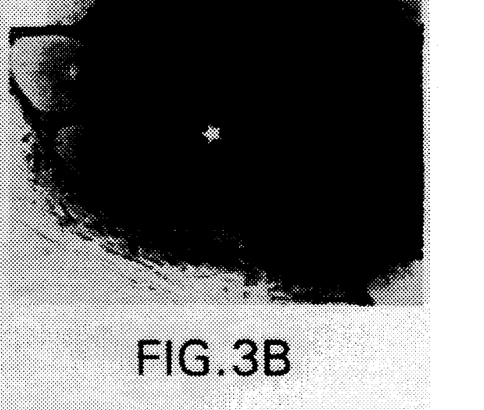
Figure 3C:
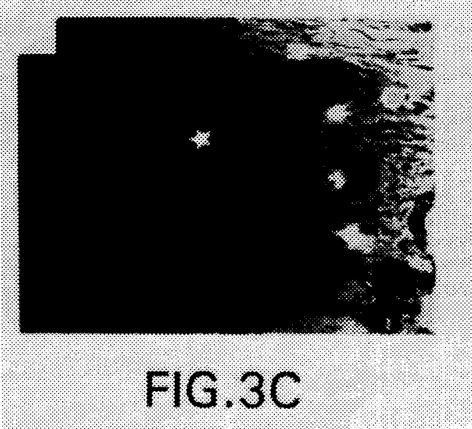
Figure 3D:
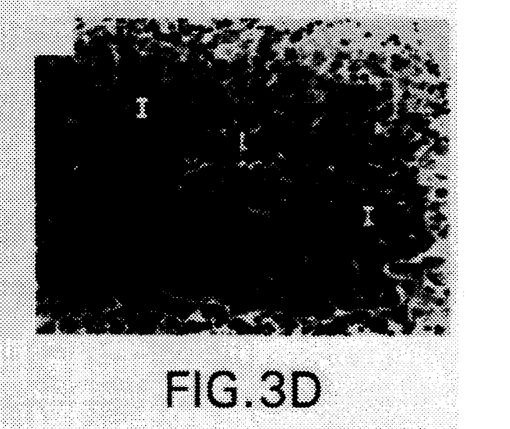
Figure 3E:
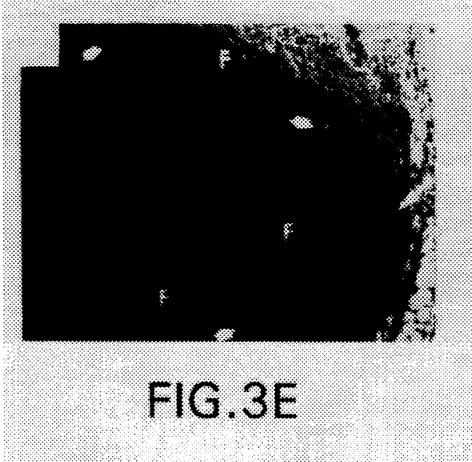
Figure 3F:
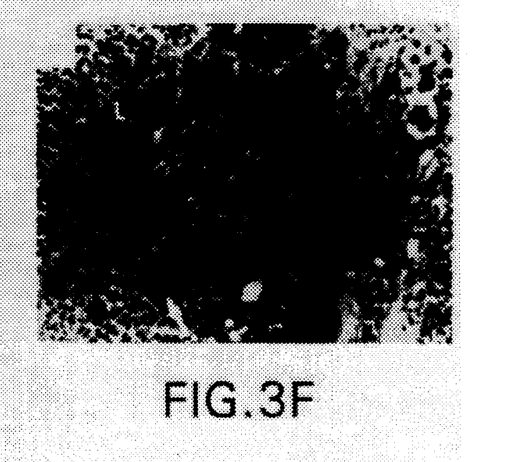

By contrast, no band of the size expected for peptide (D) could be detected at any time during the development, either in the medium or in the cellular extract after labeling with $^{35}$S-methionine and immunoprecipitation with the antiserum (cf. FIG. 2, part A). The band pattern present in the upper part of the gel persisted after a non-immune control serum had been used (lanes 7 and 15) and it did not compete on the addition of synthetic peptide (C) to the immunoprecipitation reaction (lanes 8 and 16), indicating that it corresponds to a non-specific adsorption.

The culture medium and the cellular extracts were also analyzed without immunoprecipitation subsequent to labeling with $^{35}$S-cysteine (cf. FIG. 2B, lanes 1 and 4) or with $^{35}$S-methionine (lane 5). One band (indicated by an arrow), labeled with cysteine (lane 1) but not with methionine (lane 2), was clearly visible in the culture medium and it migrated to the same level as the immunoprecipitated peptide (D) (lane 3). By contrast, there was no differential labeling in the total cellular extract, which indicates that the molecular weight of the proteins migrating to this level does not correspond to peptide (D).

The results which have just been mentioned form the basis of the hypothesis that the three methionine residues located at the amino-terminal end of the sequence of the pS2 protein deduced from cDNA belong to a signal peptide which is rapidly cleaved.

FIG. 1 shows the development with time of the labeling of peptide (D) with $^{35}$S-cysteine. Parts A and B respectively show MCF-7 cells cultivated in the presence of estradiol and phenol red and labeled with $^{35}$S-cysteine for different times: 15 minutes, 30 minutes, 1 hour, 2 hours, 4 hours and 6 hours, in lanes 1 to 6 respectively. Aliquots of the medium (200 μl) (part A) and of the cellular extracts (25 μl) (part B), corresponding to identical fractions of the total culture, were immunoprecipitated and then analyzed on a gradient of 15 to 25% of SDS-polyacrylamide gel and by fluorography. M denotes molecular weight markers. Part C shows labeling for 16 hours with $^{35}$S-cysteine; lane 2: the immunoprecipitate of an aliquot of medium; lane 1: same as lane 2, but in the presence of competing synthetic peptide (C).

FIG. 2, part A, shows an attempt to label peptide (D) with $^{35}$S-methionine in the medium (lanes 1 to 8) and the cellular extract (lanes 9 to 16). The experiment is the same as in FIG. 1, but in the presence of $^{35}$S-methionine. Lane 0 is identical to lane 5 of FIG. 1A and the labeling times were 15 minutes, 30 minutes, 1 hour, 2 hours, 3 hours, 4 hours and 6 hours, as indicated. The immunoprecipitation was carried out with non-immune serum (lane 7 for the medium and lane 15 for the cellular extract) or in the presence of immune serum and competing synthetic peptide (C) (lane 8 for the medium and lane 16 for the cellular extract). M denotes molecular weight markers.

Part B: peptide (D) can be detected direct in the medium. The synthesis of the protein by MCF-7 cells was carried out in the presence of $^{35}$S-cysteine (lanes 1 and 4) or $^{35}$S-methionine (lanes 2 and 5). The cells were cultivated in the presence of phenol red and estradiol and labeled for a period of 6 hours. Aliquots of medium and of cellular extracts, containing the same number of precipitable counts of TCA, were analyzed direct on a gradient of 15 to 25% of SDS-polyacrylamide gel. Lanes 1 and 2: culture medium; lanes 4 and 5: cellular extracts. Lane 3 and the arrow: immunoprecipitated pS2 protein labeled in vivo with $^{35}$S-cysteine.

Part C: an attempt to label peptide (D) with $^{14}$C-leucine. MCF-7 cells cultivated in the presence of estradiol and phenol red were labeled for a period of 6 hours with $^{14}$C-leucine. 200 μl aliquots of culture medium (lane 2) or of cellular extracts (lane 3) were immunoprecipitated as in FIGS. 1 and 2A. Lane 1 and the arrow give the position of the immunoprecipitated peptide (D) labeled in vivo with $^{35}$S-cysteine. Film exposure: two months.

EXAMPLE 7

Sequencing of peptide (D) isolated from MCF-7 cells (pS2M)

After reduction and alkylation of the cysteines to the form of S-(β-pyrid-4-ylethyl)cysteine by FRIEDMANN's method, followed by degradation with trypsin, 6 major peptides are obtained which are separated by chromatography on C8 reversed phase.

The cysteines are distributed in the protein in such a way that each peptide obtained by trypsin degradation contains at least one S-(β-pyrid-4-ylethyl)cysteine, which is determined at a wavelength of 254 nm.

Figure 5:
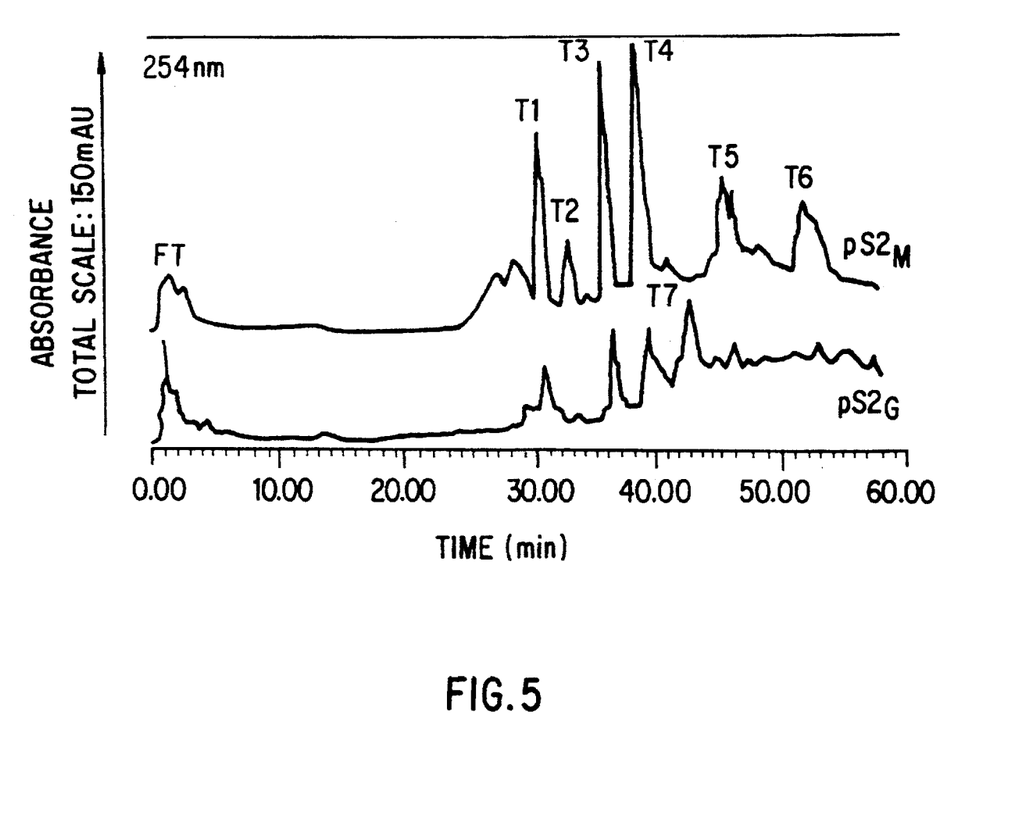
FIG. 5 is a C8 reversed phase chromatogram showing the major peptides obtain following degradation with trypsin.

The method gives 6 trypsin fragments, called T1 to T6 (FIG. 5, upper curve).

FIG. 5 shows the fractionation of the trypsin peptides of peptide (D) isolated from gastric juice (pS2G) and from MCF-7 cells (pS2M), carrying S-(β-pyrid-4-ylethyl) cysteine residues, by chromatography on an Aquapore Brownlee RP300 microbore column (7μC8/2.1×30 mm) equilibrated with a buffer composed of a 0.1% solution of TFA (trifluoroacetic acid, pH 2). The columns are eluted in 60 minutes with a gradient of 0 to 80% of buffer B, which is composed of acetonitrile containing 0.1% of TFA. The throughput of the column is 0.1 ml/min. and the different peptides are detected by their absorbance at 254 nm as a function of the time at which they appear.

Figure 6:
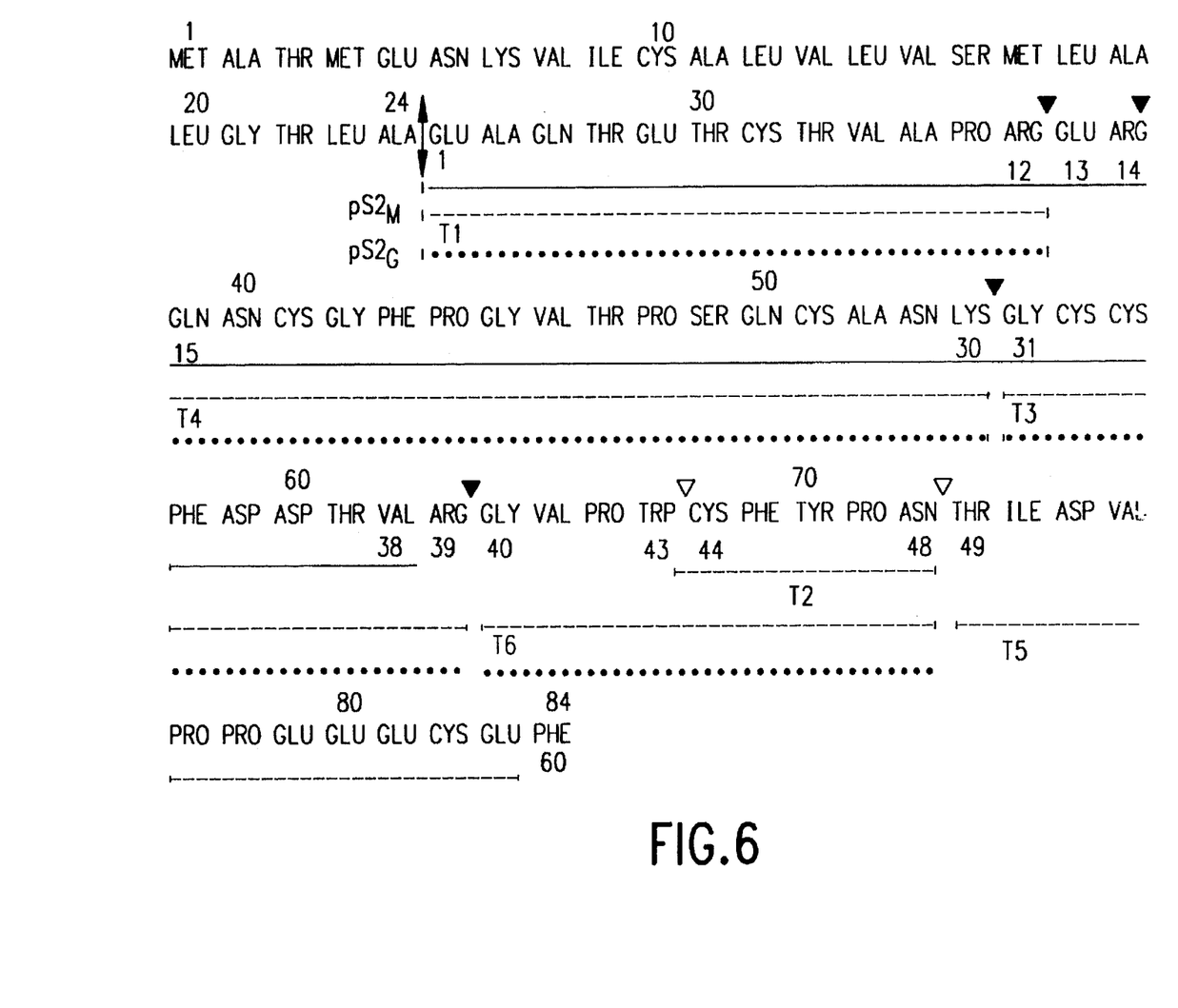
FIG. 6 shows the sequence of the pS2 protein, indicating the sites of cleavage by a signal peptidase, which gives rise to peptide (D).

These trypsin peptides were sequenced to give the map of peptide (D) isolated from MCF-7 cells (FIG. 6).

FIG. 6 shows the sequence of the pS2 protein, indicating the sites of cleavage by the signal peptidase (↕), which gives rise to peptide (D), the sites of cleavage by trypsin (▲) and the sites of cleavage not attributed to these two enzymes (Δ).

The sequence of this peptide makes it possible to define four sites of cleavage by trypsin, located down-stream of the basic amino acids $Arg_{36}$, $Arg_{38}$, $Lys_{54}$ and $Arg_{63}$.

The action of trypsin ought therefore to have generated the following 5 peptides: $GLU_{25}$-$ARG_{36}$, $GLU_{37}$-$ARG_{38}$, $GLN_{39}$-$LYS_{54}$, $GLY_{55}$-$ARG_{63}$ and $GLY_{64}$-$PHE_{84}$. In fact, of the 6 peaks observed, only T1, T3 and T4 correspond to predicted trypsin peptides: $GLU_{25}$-$ARG_{36}$, $GLY_{55}$-$ARG_{63}$ and $GLN_{39}$-$LYS_{54}$ respectively.

The other peaks (T2, T5 and T6) originate from unexpected cleavages:

the cleavage between $TRP_{67}$ and $CYS_{68}$ affects only 30% of the pS2M molecules and originates from contamination of the trypsin preparation with chymotrypsin;

the cleavages between $ASN_{72}$ and $THR_{73}$ originate neither from trypsin nor from chymotrypsin and are the work of a peptidase which is either cosecreted or a contaminant of the trypsin.

Moreover, the dipeptide $GLU_{37}$ $ARG_{38}$, which is too small to be retained on the column, is therefore undetected and its presence was deduced from the sequence of the unmodified protein.

Comparison of the sequence obtained by placing these trypsin peptides end-to-end, with the sequence of the unmodified protein of 84 amino acids, shows that the signal peptidase cleaves the initial protein after the ALA residue located in position 24 downstream of the N-terminal methionine. The secreted form therefore starts with the sequence GLU-ALA-GLN.

EXAMPLE 8

Sequencing of peptide (D) isolated from gastric juice (pS2G)

The protocol for reduction and alkylation of the cysteines and then for lysis with trypsin is the same for sequencing peptide (D) isolated from gastric juice (pS2G) as that used for sequencing pS2M.

Chromatography of the lyzate obtained gives a trace showing a few differences compared with that obtained in the case of pS2M.

The fragments T1, T3, T4 and T6 were sequenced and are identical in both cases.

The sequences corresponding to T2 and T5 were not found this time.

No sequence could be obtained from the additional peak T7.

The absence of peptide T2, compared with the pS2M preparation, is not in itself surprising as this peptide results from contamination.

The site of cleavage by the signal peptidase is therefore identical for the peptide isolated from two different types of cells.

A difference between pS2M and pS2G is observed as regards the GLU residue located at the N-terminal end of the protein. In fact, in the case of pS2G, this amino acid is cyclized to the form of a pyro-GLU, preventing the sequence from being established from the unmodified form. However, the N-terminal trypsin peptide could be sequenced, indicating an unblocking of this N-terminal end.

EXAMPLE 9

Immunocytochemical detection of peptide (D)
1) Preparation of histological sections A surgical sample was cut into thin slices, which were used for immunocytochemical detection of the ER's, the PR's and peptide (D). The samples intended for immunocytochemical detection of the ER's and the PR's were frozen in isopentane at −180° C., whereas the samples intended for immunocytochemical detection of peptide (D) were embedded in paraffin and fixed with 10% formalin for 24 hours.
2) Immunocytochemical staining of peptide (D)

The samples embedded in paraffin and fixed with formalin were sectioned, the paraffin was removed with toluene and the samples were rinsed perfectly with absolute ethanol. After washing with water and PBS, the sections were incubated with sheep serum (2.5% in PBS containing 0.5% of bovine gammaglobulins) to reduce the non-specific staining. After incubation with antipeptide rabbit polyclonal antibodies (at a concentration of 1:640), the sections were incubated successively with anti-rabbit sheep IgG's and then with a rabbit peroxidase-antiperoxidase system at a concentration of 1:10 for the IgG's and 1:50 for the peroxidase-antiperoxidase system. Each incubation was followed by washing with PBS. After a final rinse with PBS, the sections were incubated with DAB and stained with hematoxylin at a concentration of 1:10. The immunocytochemical determinations of the ER's and the PR's were carried out on frozen sections using monoclonal antibody kits supplied by Abbot and Transbio respectively, in accordance with the procedure recommended by these suppliers. The intensity of the stain was estimated on a 4-point scale (0 to 3+) and the proportion of positively stained tumoral cells was determined as a percentage of the total tumoral cells (1 to 100%); the staining index was obtained by multiplying the percentage of stained cells by the staining score (1 to 300).

3) The peptide (D) staining test was found to be cytoplasmic both on sections of breast cancer cells and on sections of metastatic nodes (cf. FIG. 3, parts A, E and F). However, the cytoplasmic distribution of the stain was not uniform and frequently showed perinuclear condensation (cf. arrow in FIG. 3, part F), which may correspond to the GOLGI apparatus, since it is known that peptide (D) is secreted. Moreover, the intensity of the stain was found to be variable from one cell to another, even within a given area of a section (cf. FIG. 3A and F). The same also applied to the specific nuclear staining of the ER's (FIG. 3B). However, not all the breast carcinomas were found to be positive vis-A-vis the specific staining of peptide (D) (FIG. 3D). The staining was found to be specific for peptide (D), as demonstrated by the fact that it was suppressed when placed in competition with one of the synthetic peptides used to raise the antibodies; in the present case, this peptide was peptide (C) comprising 31 amino acids (FIG. 3, part C). Furthermore, cells of normal ductular epithelium ("N" in FIG. 3) and of benign breast tumors were not stained.

Figure 4:
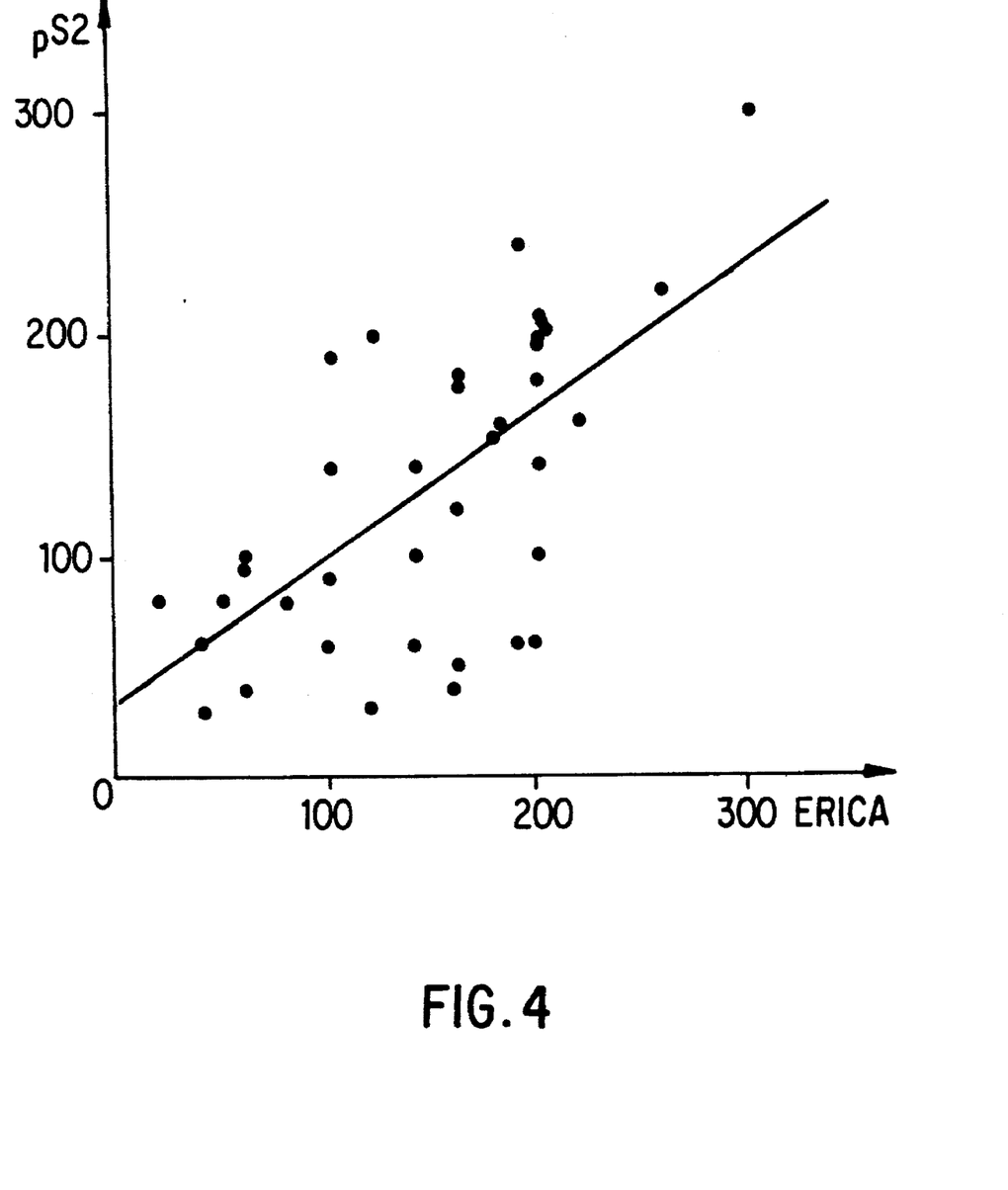
FIG. 4 shows the correlation between the staining index of peptide (D) and the staining index of the estrogen receptors.

A good correlation was observed between the staining index of peptide (D) and the intensity score of pS2 mRNA, determined from the NORTHERN blot analysis of RNA previously described in the literature, which indicates that the presence of peptide (D) very probably reflects increased transcription, as already demonstrated previously in the literature using the MCF-7 breast cancer cell line. The fact that this induction is ER-independent is strongly supported by the good correlation which exists between the staining index of peptide (D) and the staining index of the ER's (cf. FIG. 4 and Table I attached). The conclusion which can be drawn from this is that the expression of the pS2 gene in breast cancers is very probably estrogen-dependent, as is the case in the MCF-7 cell line.

EXAMPLE 10

Comparative expression of the pS2 gene with those of the estrogen and progesterone receptors and the erbB-2 oncogene Table I attached represents a summary of the results obtained for 180 breast cancer samples for which all the parameters were determined unequivocally, with few exceptions, as regards the expression of the ER's (estrogen receptors), the PR's (progesterone receptors), the pS2 gene (pS2) and the erbB-2 oncogene. The proportions of ER's and PR's were determined using all the following assays: ER-DCC, PR-DCC, ER-ICA and PR-ICA, except for 2 of the 7 cases, namely ER(+),PR(−) and pS2(+), for which the PR's were tested only by PR-DCC [DCC=dextran-coated charcoal steroid binding assay; ICA=immunocytochemical assay]. The expression of the ps2 gene was determined using both analysis with the aid of pS2 mRNA, and pS2-ICA. The excess expression (positiveness) and the undetectable or very small levels of expression (negativeness) of the erbB-2 gene were determined by analysis with the aid of mRNA. The distribution of the metastases of the axillary lymph nodes (ALN) is indicated in the last column to the right of Table I. ER(+) and PR(+) correspond to samples which were found to be positive using at least one of the ER and PR tests; pS2(+) corresponds to positive samples for tests using pS2 mRNA and/or the immunocytochemical assay for pS2 (and usually for both) and excess expression for erbB-2-(+) was determined by analysis with the aid of mRNA.

TABLE I

ALN(+) indicates the presence of at least one metastasized node.

The percentages indicated in round brackets refer to the total number of tumors (180 cases), while the percentages in square brackets refer either to ER(+) tumors (129 cases, upper part of Table I) or to ER(−) tumors (51 cases, lower part of Table I).

All breast cancers can be categorized in six subclasses of unequal importance, as shown in Table I. 72% of tumors are ER(+), 88% of these being PR(+) and 12% PR(−). However, not all PR(+) cancers are pS2(+) and not all PR(−) cancers are pS2(−). In fact, only 62% of ER(+) tumors were also found to be positive for the expression of PR and pS2, whereas 26% of ER(+) tumors were found to be PR(+) and pS2(−). It was also found that a few ER(+),PR(−) tumors were either pS2(+) or pS2(−). These observations are of great interest considering that the transcription of both the PR gene and the pS2 gene can be induced by an estrogen in MCF-7 cells. Thus the simultaneous determination of the expression of the ER, PR and pS2 genes reveals an additional functional heterogeneity in ER(+) breast cancers. This may reflect either a heterogeneity of the ER's themselves, which would be capable of inducing both the PR gene and the pS2 gene or neither of them, or a heterogeneity in the ability of the PR and pS2 genes to respond to estrogens. On the other hand, ER(−) cancers appear to be very homogeneous as regards the expression of PR and pS2, since 96% of them express neither of these two genes inducible by an estrogen. The excess erbB-2 expression was also distributed among the various subclasses. It should be emphasized that the immunocytochemical determination of the ER's, the PR's and peptide (D) is very useful for examining the heterogeneity of tumors as regards their response to estrogens and, consequently, the suitability of breast cancers for treatment by hormonotherapy.

EXAMPLE 11

Determination of peptide (D) on cytosol

The cytosol is prepared from specimens taken from breast tumors, by biopuncture or by tissue grinding, the specimens being frozen in 10 mM Tris buffer containing 1.5 mM EDTA, 10 mM monothioglycerol and 10 mM sodium molybdate, pH 7.4, as described for the determinations of hormone receptors, which dispenses with specific preparation of the cytosol and makes it possible to determine peptide (D) in addition to the receptors already routinely determined.

As is apparent from the foregoing description, the invention is in no way limited to those methods of execution, embodiments and methods of application which have now been described more explicitly; on the contrary, it encompasses all the variants thereof which may occur to those skilled in the art, without departing from the framework or the scope of the present invention.

What is claimed is:

1. An isolated and purified peptide consisting of the following amino acid sequence D:

```
                         30
GLU ALA GLN THR GLU THR CYS THR VAL ALA PRO
                         40
ARG GLU ARG GLN ASN CYS GLY PHE PRO GLY VAL
THR PRO SER GLN CYS ALA ASN LYS GLY CYS CYS
            60
PHE ASP ASP THR VAL ARG GLY VAL PRO TRP CYS
        70
PHE TYR PRO ASN THR ILE ASP VAL PRO PRO GLU
GLU GLU CYS GLU PHE.
```

* * * * *

UNITED STATES PATENT AND TRADEMARK OFFICE
CERTIFICATE OF CORRECTION

PATENT NO. : 5,635,596
DATED : JUNE 3, 1997
INVENTOR(S) : CHAMBLON, ET AL.

It is certified that error appears in the above-identified patent and that said Letters Patent is hereby corrected as shown below:

Column 1, line 26, "since 1896"

should read --since 1986--.

Column 4, line 2, "84 amine"

should read --84 amino--.

Column 4, line 45, "3a-F"

should read --3A-F--.

Column 5, line 28, "LYS$_4$,"

should read --LYS$_{54}$,--.

Column 13, line 34, "peptide (c)"

should read --peptide (C)--.

UNITED STATES PATENT AND TRADEMARK OFFICE
CERTIFICATE OF CORRECTION

PATENT NO. : 5,635,596
DATED : JUNE 3, 1997
INVENTOR(S) : CHAMBLON, ET AL.

It is certified that error appears in the above-identified patent and that said Letters Patent is hereby corrected as shown below:

Column 18, line 4, "*vis-A-vis*"

should read --*vis-à-vis*--.

Column 18, line 47, "ps2"

should read --pS2--.

Column 22, Claim 1, line 20, the first occurrence "GLU"

should read --80--.
GLU

Signed and Sealed this

Sixth Day of October, 1998

Attest:

BRUCE LEHMAN

*Attesting Officer*  *Commissioner of Patents and Trademarks*